(12) United States Patent
Teixeira et al.

(10) Patent No.: US 10,849,585 B1
(45) Date of Patent: Dec. 1, 2020

(54) ANOMALY DETECTION USING PARAMETRIZED X-RAY IMAGES

(71) Applicant: Siemens Healthcare GmbH, Erlangen (DE)

(72) Inventors: Brian Teixeira, Verneuil-en-Halatte (FR); Vivek Kumar Singh, Princeton, NJ (US); Birgi Tamersoy, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 16/540,322

(22) Filed: Aug. 14, 2019

(51) Int. Cl.
| | | |
|---|---|---|
| *G06K 9/00* | (2006.01) | |
| *A61B 6/00* | (2006.01) | |
| *A61B 5/055* | (2006.01) | |
| *G06N 3/04* | (2006.01) | |
| *G06N 20/00* | (2019.01) | |
| *G06N 3/08* | (2006.01) | |
| *G06T 7/514* | (2017.01) | |
| *G06T 11/00* | (2006.01) | |
| *A61B 5/05* | (2006.01) | |
| *G06K 9/62* | (2006.01) | |
| *A61B 5/00* | (2006.01) | |
| *G06T 7/70* | (2017.01) | |
| *G06T 7/00* | (2017.01) | |

(52) U.S. Cl.
CPC ............ *A61B 6/5205* (2013.01); *A61B 5/055* (2013.01); *A61B 5/0515* (2013.01); *A61B 6/463* (2013.01); *G06N 3/0445* (2013.01); *G06N 3/08* (2013.01); *G06N 20/00* (2019.01); *G06T 7/514* (2017.01); *G06T 11/003* (2013.01); *A61B 5/0033* (2013.01); *A61B 6/545* (2013.01); *G06K 9/6262* (2013.01); *G06K 9/6274* (2013.01); *G06K 2209/055* (2013.01); *G06N 3/0454* (2013.01); *G06T 7/0014* (2013.01); *G06T 7/70* (2017.01); *G06T 2207/10028* (2013.01); *G06T 2207/10116* (2013.01); *G06T 2207/20081* (2013.01); *G06T 2207/20084* (2013.01)

(58) Field of Classification Search
None
See application file for complete search history.

(56) References Cited

U.S. PATENT DOCUMENTS

2015/0146858 A1* 5/2015 Omote .................. G01N 23/20 378/74
2019/0057521 A1 2/2019 Teixeira

* cited by examiner

*Primary Examiner* — Atiba O Fitzpatrick (57) ABSTRACT

For anomaly detection based on topogram predication from surface data, a sensor captures the outside surface of a patient. A generative adversarial network (GAN) generates a topogram representing an interior anatomy based on the outside surface of the patient. An X-ray image of the patient is acquired and compared to the generated topogram. By quantifying the difference between the real X-ray image and the predicted one, anatomical anomalies may be detected.

20 Claims, 3 Drawing Sheets

ANOMALY DETECTION USING PARAMETRIZED X-RAY IMAGES

BACKGROUND

The present embodiments relate to detecting anomalies using parametrized X-ray images and using parametrized X-ray images to augment training data. Acquiring a large number of X-ray images for deep learning may be difficult due to the exposure of patients to radiation. Recently developed deep learning algorithms require large amount of data for training. Most common methods for augmenting training data are based on alteration of images, such as image rotation, image translation, warping, rescaling, etc. While these methods are useful, they face the problem of requiring multiple points of view for a given image, and thus a given patient, rather than augmenting the data at the patient level.

SUMMARY

The scope of the present invention is defined solely by the appended claims, and is not affected to any degree by the statements within this summary. Systems, non-transitory computer readable storage media, and methods are provided for anomaly detection based on a comparison of a generated topogram with acquired X-ray images. A sensor captures the outside surface of a patient. A topogram representing interior organs is generated based on the outside surface of the patient. The topogram generated may be generated by a generative adversarial network (GAN). Internal landmarks are used in the topogram prediction to generate a full topogram image from an incomplete or partial topogram image and to generate meaningful perturbations of topogram images. For generating training data, the generated topogram may be altered based on the internal landmarks identified in the topogram.

In a first aspect, a method is provided for anomaly detection in a medical imaging system using a topogram. The topogram represents an internal anatomy of the patient as a projection through the patient. A sensor captures surface data of a patient. The surface data represents an outer surface of the patient. An image processor generates the topogram by a machine-learned network in response to input of the surface data to the machine-learned network. The machine-learned network is trained with surface data from healthy patients. An X-ray image of the patient is acquired. The image processor compares the generated topogram with the acquired X-ray image. The image processor then detects an anomaly of the patient from the comparison between the generated topogram and the acquired X-ray image.

The sensor may be a depth sensor. The sensor may also be a camera where the surface data includes optical measurements. A statistical shape model is fitted to the surface data. The surface data includes depths from the fit statistical shape model and a projection of the outer surface or a thickness. The machine-learned network is trained as a machine-learned generative adversarial network including a fully convolutional network with an encoder and a decoder. The generated topogram is a parametrized image having a plurality of predicted body markers. The plurality of predicted body markers represents spatial parameters of the internal anatomy of the patient.

The image processor regenerates the topogram based on the plurality of predicted body markers. The plurality of predicted body markers are adjusted such that the generated topogram matches the acquired X-ray image where the generated topogram and the acquired X-ray image overlap. The adjustment is done based on comparing the generated topogram with the acquired X-ray image. The image processor regenerates the topogram using the adjusted body markers.

The machine-learned network generates perturbations of the generated topogram as training data. To generate the perturbations, an internal landmark of the generated topogram is annotated. A random perturbed position of a first predicted body marker of the plurality of predicted body markers is created by moving the first predicted body marker along an image manifold. A changed position of the annotated internal landmark is propagated based on the random perturbed position of the first predicted body marker. The image processor generates a random perturbed parametrized image based on the changed position of the annotated internal landmark and the random perturbed position of the first predicted body marker. The creating, propogating, and generating are repeated for different random perturbed positions to create a predetermined number of generated random perturbed parametrized images associated with the annotated internal landmark of the generated topogram. The annotating, the creating, the propagating, and the generating are repeated a predetermined number of times for a predefined number of generated topograms. The changed position of the annotated internal landmark is propagated by using coefficient normed template matching.

In a second aspect, a method is provided for detecting anatomical anomalies in a medical imaging system. A sensor captures surface data representing an outer surface of a patient. An image processor generates a spatial marker map by a first machine-learned network. The first machine-learned network outputs the spatial marker map in response to input of the surface data to the first machine-learned network. The image processor generates a topogram by a second machine-learned network in response to input of the surface data and the spatial marker map to the second machine-learned network. The topogram represents an internal anatomy of the patient as a projection through the patient. An X-ray image of the patient is acquired. The image processor compares the generated topogram with the acquired X-ray image. The image processor then detects an anatomical anomaly between the generated topogram and the acquired X-ray image.

In a third aspect, a medical imaging system is provided for anatomical anomaly detection. A memory is configured to store surface data of a patient and a plurality of topograms. Each topogram of the plurality of topograms are associated with corresponding surface data of other patients. An image processor is configured to generate a predicted patient topogram based on the surface data of the patient and the plurality of topograms. The image processor is also configured to acquire an X-ray image of the patient and compare the generated predicted patient topogram with the acquired X-ray image. The image processor is configured to detect, based on the comparison, an anatomical anomaly between the generated predicted patient topogram and the acquired X-ray image. A display is configured to display the detected anatomical anomaly.

The image processor matches the surface data of the patient to the corresponding surface data of other patients associated with the plurality of topograms. The image processor predicts the patient topogram based on the matched surface data. The plurality of stored topograms correspond to a class defined by health patients. The image processor may also generate the predicted patient topogram by a machine-learned network in response to input of the surface data of the patient and the plurality of topograms to the machine-learned network.

Any one or more of the aspects described above may be used alone or in combination. These and other aspects, features and advantages will become apparent from the following detailed description of preferred embodiments, which is to be read in connection with the accompanying drawings. The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the embodiments. Moreover, in the figures, like reference numerals designate corresponding parts throughout the different views.

DETAILED DESCRIPTION OF EMBODIMENTS

Embodiments disclosed herein address challenges associated with the amount of data needed to train machine learning algorithms. The proposed solution presents a system to augment training data using deep machine learning algorithms. The proposed method augments the data by controlling the internal anatomy of one patient to generate new synthetic patients that can be used to train machine learning algorithms. Embodiments disclosed herein address the problem of missing data or lack of variance in training datasets. Embodiments disclosed herein augment training data by completing partial topogram images (or regenerating entire topogram images), generating meaningful perturbations of topogram images, and detecting and fixing anomalies in data.

The proposed method augments training data using parametrized images. A pipeline for generating parametrized images, meaning images that may be modified by adjusting a set of sparsely distributed body markers, is disclosed in U.S. Patent Application Publication No. 2019/0057521 ("the '521 application), filed Jul. 20, 2018, the entirety of which is hereby incorporated by reference. Using the method described in the '521 application, the proposed architecture predicts a phantom topogram image together with a set of body landmarks describing important organs (heart, lungs, liver, kidney, etc.) from the patient body surface data. In this way, the predicted body markers represent spatial parameters of the internal anatomy of the patient. Given the body skin surface, embodiments disclosed herein can use the pipeline of parametrized images to get a synthetic topogram together with body landmarks. The topogram and landmarks are strongly correlated. When updating the landmarks, a new topogram image can be generated that matches the given landmarks. The landmarks may then be adjusted to control the internal patient anatomy represented by the topogram. The result is a pipeline that generates data (i.e., synthetic topograms) used to train machine learning algorithms.

Body markers, or landmarks, may be predicted, allowing adjustment to update the X-ray image. With the proposed framework, synthetic X-ray images may easily be generated by varying surface geometry. By perturbing the parameters, additional synthetic X-ray images may be generated from the same surface geometry. As a result, the training data barrier in the medical domain is overcome by producing many X-ray images through parameter adjustment. Since the markers serve as spatial parameters to perturb the image, the predicted image of the internal anatomy is a parametrized image. The predicted topogram may be manipulated using body markers distributed across the body. For example, if the predicted lung appears short, then a body marker near the lung region may be manipulated to adjust its position, and the topogram will be updated in a physically consistent manner.

The proposed pipeline of training data has the ability to capture the non-linear correlation between the surface data of the patient, the internal landmarks and the corresponding topogram image. As a result, topograms are parametrized with both the surface data and the landmarks. For efficient training, the 3D surface data is represented as a 2-channel 2D image.

The proposed method for augmenting training data is a learning-based method, trained using deep learning on more than 2000 real X-ray images, ensuring realism in the augmented data. Moreover, the proposed approach directly learns at the patient level by modifying the patient's internal anatomy, rather than working on the image level. Such an approach better addresses the problem of missing training data and is helpful for training other deep neural networks. Finally, the proposed approach has an important number of control points and can represent a large variety of internal anatomy configurations. As shown below, the proposed method of data augmentation via parametrized images outperforms classic data augmentation strategies such as translations.

While the proposed method represents different configurations of the internal body anatomy using a learning-based method, warping may also be used to modify the X-ray images representing the patient's internal anatomy. However, such an approach may not guarantee that the generated images would be plausible, while the proposed approach ensures realism of synthetic data using machine trained networks, such as Generative Adversarial Networks.

The predicted topogram may be useful for teaching purposes, such as generating topogram images as samples to be used in machine training to avoid a data barrier of too few samples for training. The predicted topogram may be used for scan planning. For example, the generated topogram is used for more precise positioning compared to just using body markers. Furthermore, positioning suggested by the system using a physically consistent generated topogram may be more readily used by radiographers as opposed to just the body marker points.

The topogram may be used for detection of anomalies, patient positioning, interventional procedures, completion of a full X-ray from a partial X-ray image, or other uses. In one embodiment, the machine-learned networks of the proposed architecture is trained on healthy patients only. Thus, since the topogram is predicted from the skin surface, the generated topogram will not present any pathologies and may thus be compared to a real topogram from the patient for anomaly detection.

Computed tomography or X-ray based topogram prediction is provided in the examples below. Other modes of medical imaging may be used, such as predicting the image for magnetic resonance, positron emission tomography, single photon emission computed tomography, or ultrasound imaging.

It is to be understood that elements and features of the various representative embodiments described below may be combined in different ways to produce new embodiments that likewise fall within the scope of the present teachings.

Figure 1:
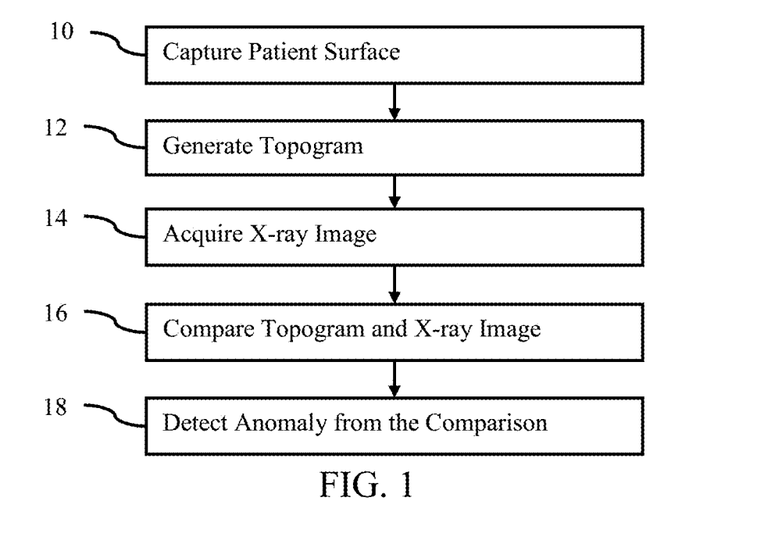
FIG. 1 is a flow chart diagram of one embodiment of a method for anomaly detection in a medical imaging system using a topogram.

FIG. 1 is a flow chart diagram of one embodiment of a method for anomaly detection in a medical imaging system using a topogram. A machine-learned network, such as a generative adversarial network (GAN) is used to generate a topogram from data representing an outside of a patient. The topogram represents an internal anatomy of the patient as a projection through the patient, such as a CT or X-ray topogram. An X-ray image of the patient is acquired. The generated topogram is compared with the acquired X-ray image. An anomaly of the patient is detected from the comparison between the generated topogram and the acquired X-ray image.

The method of FIG. 1 is performed in the order shown (e.g., top to bottom or numerical), but other orders may be used. In alternative embodiments, these acts may occur in a different sequential order and/or one or more of these acts may occur substantially contemporaneously. Additional, different or fewer acts may be provided. For example, act 10 is not provided as the patient surface data may be obtained without capturing by a sensor.

In act 10, a sensor captures first surface data representing an outer surface of a patient. The surface measurements may be obtained using RGBD sensors or 2.5D depth sensors such as Microsoft Kinect 2, ASUS Xtion Pro, or by 3D reconstructions from multiple 2D images. The depth sensor may be a camera or cameras capturing a grid projected onto the patient. Multiple cameras may reconstruct an outer surface from multiple images without transmission of structured light. Other optical or non-ionizing sensors may be used.

The sensor is directed at a patient. The sensor captures the outer surface of the patient from one or more perspectives. Any portion of the outer surface may be captured, such as the entire patient from head to toe and hand to hand on one side or just the torso or abdomen.

The outer surface is the skin of the patient. In other embodiments, the outer surface includes clothing. The sensor may use a frequency that passes through clothing and detects skin surface.

The first surface data representing an outer surface of a patient is captured as depths from the sensor to different locations on the patient, an image or photograph of the outside of the patient, or both as two channel data. The sensor outputs the sensed image and/or depths. Alternatively, the sensor measurements are processed to determine the first surface data, such as stereoscopically determining the outer surface from camera images from different angles with image processing.

The measurements of the outer surface from the sensor are the first surface data for the patient. In one embodiment, the first surface data is optical measurements when captured with a camera. In another embodiment, the measurements or other output of the sensor are used to determine the first surface data. The output is processed to determine the first surface data. For example, a statistical shape model is fit to the depths. The statistical shape model is a mesh or other representation of an average or other statistical representation of an outside of a human or part of a human. The statistical shape model includes probabilities or other constraints on alteration, so that the fitting maintains the shape based on statistics. The first surface data is then determined from the fit statistical shape model, such as depths from a point to the model.

The surface data may include different representations of the patient, such as the depths from the fit model and a projection of the outer surface (e.g., a camera image) or a thickness. The thickness may be a difference of a given depth from the maximum and minimum depth for the model or the depths from the sensor. For example, given a 3D surface mesh of a patient, 2D projections of the data are generated as a skin surface image and a depth image. As another example, the 3D human surface mesh data is represented with a 2-channel 2D image—the first channel stores the depth of the body surface as observed from front, and second channel stores the thickness computed by measuring the distance between the closest and furthest point as observed from front. Other surface data may be used.

In act 12, an image processor generates the topogram. The topogram image is predicted from the first surface data. The topogram shows the atlas of the internal patient anatomy. The topogram may be predicted from only the first surface data or may be predicted from the first surface data and other data, such as patient height, weight, or body mass index.

The topogram may be generated using the method disclosed in disclosed in U.S. Patent Application Publication No. 2019/0057521 ("the '521 application), filed Jul. 20, 2018, the entirety of which is hereby incorporated by reference. The first surface data with or without other data are input to a machine-learned network and scalar or display values for the topogram are output. For example, a projection image of the outer surface and depth image of the outer surface are input as two channels to the machine-learned network, which outputs a synthetic X-ray image (i.e., an X-ray projection) in response to the input. The generated topogram represents an internal anatomy of the patient as a projection through the patient. The image processor applies the machine-learned network for topogram prediction. Any inputs for which the network is trained to use are applied as an input feature vector, such as just the surface data.

The prediction of certain internal anatomical structures may assist in planning a medical scan. The generated topogram may be used to plan for scanning by any modality, such as CT, MR, fluoroscopy or ultrasound. For CT scanning, the generated topogram may be used to determine the scan range to obtain a full topogram or full CT scan, depending upon which organ needs to be scanned and how accurately the nearby structures may be predicted. The location of internal anatomical structures reflected in the generated topogram may assist is coil placement for MR scanning. For ultrasound scanning, the generated topogram may assist in the probe guidance by providing approximate position of the various organs. For fluoroscopy using dyna-CT scans, the generated topogram may be useful for positioning the patient and/or the scanner.

The machine-learned network is an image-to-image network, such as a generative part of a generative adversarial network, trained to convert surface data to a topogram. For example, the trained convolution units, weights, links, and/or other characteristics of the network are applied to the surface data and/or derived feature values to extract the corresponding features through a plurality of layers and output the topogram. The features of the input images (e.g., surface data) are extracted from the images. Other more abstract features may be extracted from those extracted features using the architecture. Depending on the number and/or arrangement of units or layers, other features are extracted from the input.

For training the machine-learned network, the machine learning network arrangement is defined. The definition is by configuration or programming of the learning. The number of layers or units, type of learning, and other characteristics of the network are controlled by the programmer or user. In other embodiments, one or more aspects (e.g., number of nodes, number of layers or units, or type of learning) are defined and selected by the machine during the learning.

In one embodiment, the machine-learned network is trained with surface data from a particular class of patients. For example, the machine-learned network may be trained using surface data from healthy patients only. In this example, the topogram generated from a machine-learned network trained with data from healthy patients only will not present pathologies, and may thus be compared to real topograms for anomaly detection. In another example, the class of patients may be defined by any other patient trait, such as age, gender, body type, or type of pathology, such as a missing lung.

Figure 3:
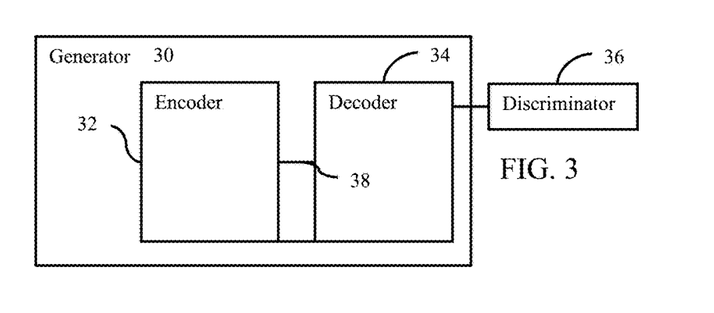
FIG. 3 is a block diagram of one embodiment of a GAN.

Any machine training architecture for outputting a spatial distribution from an input spatial distribution may be used. For example, a U-Net may be used. A convolutional-to-transposed-convolutional network may be used. One segment of layers or units applies convolution to increase abstractness or compression. The most abstract feature values are then output to another segment at a bottleneck. The other segment of layers or units then applies transposed-convolution to decrease abstractness or compression, resulting in outputting of a topogram or indication of class membership by location. FIG. 3 shows an example fully convolutional network as a GAN. The GAN includes a generator 30, such as the image-to-image or U-Net, and a discriminator 36. The generator 30 includes an encoder (convolutional) network 32 and decoder (transposed-convolutional) network 34 forming a "U" shape with a connection between passing features at a greatest level of compression or abstractness from the encoder 32 to the decoder 34. Any now known or later developed U-Net or image-to-image architectures may be used. Other fully convolutional networks may be used.

For applications, the generator 30 of the GAN is used without the discriminator 36. The GAN is applied to the patient surface data by the generator 30 without the discriminator 36. The discriminator 36 is used for training.

The GAN is a deep architecture, which may include convolutional neural network (CNN) or deep belief nets (DBN). Other deep networks may be used. CNN learns feed-forward mapping functions while DBN learns a generative model of data. In addition, CNN uses shared weights for all local regions while DBN is a fully connected network (i.e., having different weights for all regions of an image). The training of CNN is entirely discriminative through back-propagation. DBN, on the other hand, employs the layer-wise unsupervised training (e.g., pre-training) followed by the discriminative refinement with back-propagation if necessary.

The network is defined as a plurality of sequential feature units or layers. Sequential is used to indicate the general flow of output feature values from one layer to input to a next layer. The information from the next layer is fed to a next layer, and so on until the final output. The layers may only feed forward or may be bi-directional, including some feedback to a previous layer. The nodes of each layer or unit may connect with all or only a sub-set of nodes of a previous or subsequent layer or unit.

Rather than pre-programming the features and trying to relate the features to attributes, the deep architecture is defined to learn the features at different levels of abstraction based on an input image with or without pre-processing. The features are learned to reconstruct lower level features (i.e., features at a more abstract or compressed level). For example, features for reconstructing an image are learned. For a next unit, features for reconstructing the features of the previous unit are learned, providing more abstraction. Each node of the unit represents a feature. Different units are provided for learning different features.

Within a unit or layer, any number of nodes is provided. For example, 100 nodes are provided. Later or subsequent units may have more, fewer, or the same number of nodes. In general, for convolution, subsequent units have more abstraction. For example, the first unit provides features from the image, such as one node or feature being a line found in the image. The next unit combines lines, so that one of the nodes is a corner. The next unit may combine features (e.g., the corner and length of lines) from a previous unit so that the node provides a shape or building indication. For transposed-convolution to reconstruct, the level of abstraction reverses. Each unit or layer reduces the level of abstraction or compression.

The features of the nodes are learned by the machine using any building blocks. For example, auto-encoder (AE) or restricted Boltzmann machine (RBM) approaches are used. AE transforms data linearly, and then applies a non-linear rectification, like a sigmoid function. The objective function of AE is the expected mean square error between the input image and reconstructed images using the learned features. AE may be trained using stochastic gradient descent or other approach to learn, by the machine, the features leading to the best reconstruction. The objective function of RBM is an energy function. Exact computation of the likelihood term associated with RBM is intractable. Therefore, an approximate algorithm, such as contrastive-divergence based on k-step Gibb sampling, is used to train the RBM to reconstruct the image from features.

In one embodiment, the topogram prediction is treated as a classic image-to-image translation problem. Starting from 2 channel images (e.g., skin surface and depth to skin image), a single channel image of the same size (topogram image) is regressed. This approach provides a network able to capture the features in the input image to retrieve the output image, which consists, in a sense, of a more 'complete' version of the input. A Fully Convolutional Networks (FCN) may be used, such as the generator 30 with the encoder 32 and the decoder 34. The encoder 32 'encodes' the useful features of the input needed to regress the target, while the decoder 34 tries to use these features to create the targeted image.

In one embodiment, the generator 30 is a U-Net with one or more skip connections 38. The skip connections 38 pass features from the encoder 32 to the decoder 34 at other levels of abstraction or resolution than the most abstract (i.e. other than the bottleneck). Skip connections 38 provide more information to the decoding layers. A Fully Connected layer may be at the bottleneck of the network (i.e., between the encoder 32 and decoder 34 at a most abstract level of layers). The fully connected layer may make sure as much information as possible is encoded. Batch normalization may be added to stabilize the training.

In another embodiment, multiple U-Nets, generators 30 or GANs are stacked. For example, the generators 30 of multiple GANs may be stacked sequentially. The output from one GAN provides an input to the other GAN, which outputs the topogram. The initial GAN receives the surface data as an input. Stacking U-Nets as the generators 30 helps capture more details for the topogram. The patient's shape may be regressed with more details, such as details around or other lungs.

A more realistic topogram image may result from using a GAN than from a U-net or generator 30 trained without a discriminator 36. GANs generate realistic images in image-to-image translation problems. GANs train two different networks simultaneously, the discriminator 36 whose purpose is to decide whether a given image is real or fake, and the generator 30 whose purpose is to fool the discriminator 36 by making images as realistic as possible.

The basic approach for training a GAN is to update the discriminator 36 with both generated and real images, freeze weights in the discriminator 36, and then update the generator 30 based on how good the generator 30 is at fooling the discriminator 36. Weights in the generator 30 are updated while minimizing the binary cross entropy loss of the discriminator 36 where output is supposed to be always 1. In one embodiment, the GAN is trained from an initial state based on estimates. In another embodiment, the whole regressor model or generator 30 is not trained from scratch, but a previously trained generator 30 is updated by learning the missing details. The missing details may be reconstructed by adding a residual to the generated images. Therefore, a residual image with the same resolution as the generated image is learned. An element-wise sum of the residual and the generated image and an adversarial loss to update the residual are computed. The pre-trained generator 30 is not updated, and the residual network would take as an input the bottleneck of the regressor model, e.g. the encoded features at the most abstract level. In alternative embodiments, the pre-trained generator 30 is updated.

For training any of the networks, various optimizers may be used, such as Adadelta, SGD, RMSprop, or Adam. The weights of the network are randomly initialized, but another initialization may be used. End-to-end training is performed, but one or more features may be set. Batch normalization, dropout, and data augmentation may be (e.g., using batch normalization and dropout). During the optimization, the different distinguishing features are learned. The features providing an indication of flow given input medical image of anatomy or tissue are learned.

The optimizer minimizes an error or loss, such as the Mean Squared Error (MSE), Huber loss, L1 loss, or L2 loss. The Huber loss may be less sensitive to outliers in data (represented in the training set by big variations in shape). Use of Huber loss helps capture better context. The patient's shape may be regressed better. In another embodiment, an L1 loss is used to better define lungs or other organs represented in the generated topogram. Using the stacked U-Nets with L1 loss, the patient's shape and details for the lungs or other organs may be better than for Huber or L2 loss.

Once trained, the model may be applied to estimate a topogram from input surface data. The many samples in the training data (e.g., surface data and ground truth topograms) are used to learn to output the topogram. The machine learning model is trained to learn the correspondence between the surface data and the topogram.

Other information may be used in topogram prediction. In one embodiment, stacked networks are used. Rather than focus on topogram regression in two GANs, the stacked network uses at least one GAN to predict one or more internal body markers. External body markers may be detected or predicted. The input surface data as well as the predicted internal body markers are used to predict topogram by another GAN. The predicted body markers may be adjusted, which would automatically update the topogram.

In one embodiment, the first GAN may be a body marker prediction network that takes the surface image as input and predicts the locations for all the body markers. The resulting landmark image is a heatmap, or spatial marker map, corresponding to 17 anatomically meaningful landmarks, such as lung top, liver top, kidney center, etc.). Any number of meaningful landmarks may be used. The heatmap is a spatial distribution of likelihood of any given pixel or voxel being the landmark. For the heatmaps, each output channel compares with the given ground truth that includes a Gaussian mask (kernel radius=5, $\sigma$=1) centered at the given target location. Other radii and standard deviations may be used. Other images or spatial distributions than a heatmap may be used, such as providing binary labels for each landmark. The second GAN in a stacked network example may be an image generation network that takes the surface image and marker heatmaps as input and outputs the synthetic X-ray image as the topogram. In another embodiment where the first and second GANs are used iteratively, the first GAN may take the surface image as well as the predicted X-ray image, or topogram, as input in order to output the spatial marker map.

Referring again to FIG. 1, an X-ray image is acquired in act 14. The X-ray image may be acquired by an X-ray device coupled to the medical imaging system. In this embodiment, the X-ray image is acquired by the X-ray device capturing the X-ray image of the patient. The X-ray image may also be acquired by accessing the X-ray image from a stored location, such as in an internal or external memory. The X-ray image may be captured by an X-ray device contemporaneously with capturing the first surface data of act 10 and/or with generating the topogram of act 12. In another embodiment, the X-ray image may be captured by the X-ray device prior to act 10 (i.e., prior to the beginning of the proposed method).

In act 16, the generated topogram of act 12 is compared to the X-ray image acquired in act 14. The image processor may perform the comparison. More details of the comparison is discussed below with respect to FIG. 2.

In act 18, an anomaly of the patient from the comparison between the topogram generated in act 12 and the X-ray image acquired in act 14 is detected. The detection may be performed by the image processor based on the aforementioned comparison. The predicted topogram generates a representation of healthy anatomy learned from healthy patients. A real or actual X-ray image of the patient may be compared with the predicted topogram. By quantifying the difference between the real X-ray image and the predicted one, anatomical anomalies may be detected. For example, a missing lung or an added implant, such as a leg implant, are highlighted by subtraction.

In one embodiment, the image processor may detect an anomaly using now known or later developed thresholding methods. For example, a predefined or user-selected threshold value is set, and the image processor detects groups of connected pixels above the threshold value in each of the generated topogram and the acquired X-ray. The image processor may then threshold by size, where any region of a certain size of connected pixels having a predefined difference between the generated topogram and the acquired X-ray image are detected as an anomaly. In another embodiment, the anomaly detection may be a manual process. For example, the image processor may cause the generated topogram and the acquired X-ray image to be displayed or cause the difference between the two to be output or displayed, and a user, such as a radiologist, may detect anomalies present in the displayed or output difference.

Figure 2:
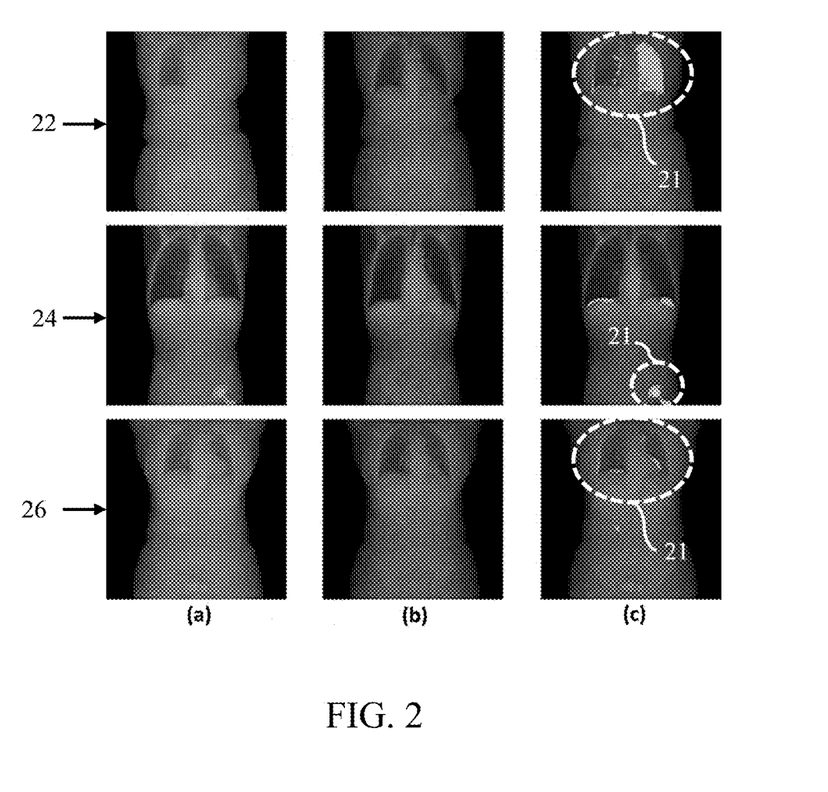
FIG. 2 illustrates examples of detection of anomalies from a comparison between an acquired real X-ray of a patient and generated predicted topogram of the patient.

FIG. 2 illustrates acts 16 and 18 of FIG. 1. Specifically, FIG. 2 illustrates the detection of anomalies 21 from a comparison between an acquired real X-ray of a patient, column (a), and a generated predicted topogram of the patient, column (b). As the proposed method generates a representation of healthy anatomy learned from healthy patients, it can be applied for anomaly detection by quantifying the difference between a real X-ray image and a predicted one. FIG. 2 illustrates such examples, where a first patient 22 has a missing lung, a second patient 24 has a leg or hip implant, which is sometimes overlooked by technicians, and a third patient 26 has no pathologies (i.e., the third patient 26 is a healthy patient). While the anatomical anomaly may be easier to identify, the proposed approach with higher resolution imaging can potentially be used to suggest candidates for lung nodules (in a chest X-ray) or other pathological conditions. Detection of anatomical anomalies may also allow selection of training criteria based on particular pathologies. For example, for a given training set, detecting missing lungs may allow a network to be trained only on patients with missing lungs, or to use the synthetic topogram instead for patients presenting this particular pathology.

In the example shown in FIG. 2, an anomaly 21 of each of the patients 22, 24, 26 is detected in a resulting image, column (c), by comparing and using the difference between the acquired, or real, X-ray (a) and generated topogram, or the predicted X-ray, (b), the difference being indicative of the anomaly 21. The difference may be achieved by subtraction. In this embodiment, a difference threshold is set to 10%. Other thresholds may be used. As shown in FIG. 2, the detected anomaly 21 of a missing lung, based on the aforementioned comparison, is shown for patient 22. Similarly, the detected anomaly 21 of a leg or hip implant, based on the comparison, is shown for patient 24. Since patient 26 is a healthy patient having no pathologies, the difference between the real X-ray and the predicted one is minor.

The proposed method is beneficial in that it allows potential issues (i.e., anomalies of internal anatomies) to be caught that normally may go undetected. For example, as mentioned above, certain implants may be overlooked by technicians. However, using the proposed method of anomaly detection, the implant is highlighted in an image resulting from the comparison between a real and predicted X-ray. This provides an improvement in identifying pathologies in medical imaging.

As radiation exposure is considered harmful, topogram images are often acquired with a limited field of view, only covering a certain body region (e.g., thorax or abdomen). Using parametric images, the topogram image of the entire body or greater region of the body may be reconstructed or predicted such that the predicted topogram is consistent with the partial yet real image. The reconstructed, or regenerated, topogram may be used for acquisition planning in subsequent or future medical scans. Using the reconstructed topogram, the scan region may be specified more precisely, thus potentially reducing the radiation exposure.

Figure 4:
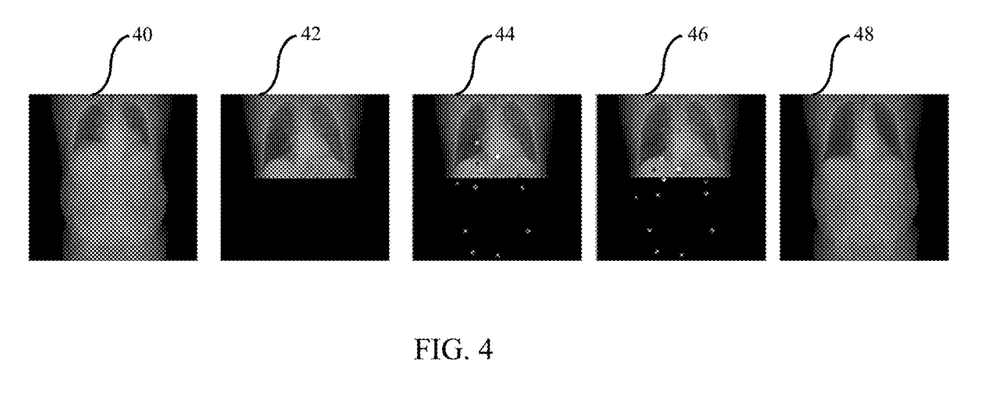
FIG. 4 illustrates examples of regenerated topograms using a parametrized image with predicted body markers and an acquired X-ray image.

To reconstruct a complete X-ray, or to regenerate the generated topogram, a parametrized topogram image of the patient is generated from the surface data. The predicted topogram may not always correspond to the true internal anatomy. This, however, may be addressed using the markers on the parametrized image by adjusting the markers such that the synthetic or generated topogram matches the real X-ray image where they overlap. The body markers may be manipulated to adjust its position. For example, body markers may be repositioned to better align with the anatomy of the real X-ray image. The markers may be moved manually. Alternatively, the generated topogram and the acquired/real X-ray may be aligned using image transformation, such as translation, rotation, projection, and/or scaling. In this case, the markers may be moved automatically by the image processor to align the markers of the generated topogram with the anatomy of the acquired X-ray image. Other now known or later developed image transformation techniques may be used.

Once the markers are adjusted, the complete topogram is regenerated together with all the markers. Once the body markers are manipulated to adjust their position, the topogram may be updated in a physically consistent manner. For example, a new spatial marker map that includes the entire set of updated body markers may be input into the machine-learned network in order to generate a new, complete topogram.

FIG. 4 illustrates regenerating a topogram using a parametrized image with predicted body markers and an acquired X-ray image. In this example, the generated topogram 40 (i.e., X-ray predicted from the surface data) does not match the partial ground truth 42 (i.e., real X-ray image). The determination that the generated topogram 40 and the real X-ray 42 do not align correctly may be performed manually. For instance, a radiologist may view the two images and determine that they do not match. Alternatively, the image processor may make this determination automatically using image processing, or thresholding, techniques, such as those discussed above for detecting anomalies. The partial ground truth X-ray 42 may be used to adjust some of the originally predicted body markers 44. Given that the generated topogram is a parametrized image having a plurality of predicted body markers, the plurality of predicted body markers may be adjusted 46, based on the comparison of the generated topogram 40 with the acquired X-ray image 42, such that the generated topogram 40 matches the acquired X-ray image 42 where the generated topogram 40 and the acquired X-ray image 42 overlap. The adjusted body markers 46 may be used to regenerate the topogram 48 (i.e., newly generated predicted X-ray image). The body markers may be adjusted manually. Alternatively, the body markers may be adjusted using image transformation, such as translation, rotation, projection, and/or scaling. In this case, the markers may be moved automatically by the image processor to align markers of the generated topogram 40 with the anatomy of the acquired X-ray image 42. Other now known or later developed image transformation techniques may be used.

Table 1 below shows the quantitative comparison between the predicted synthetic topogram 40 and markers, before and after being refined, or adjusted, using the real topogram image 42, as discussed above.

TABLE 1

|  | MAE | MSE | Δ | Δy |
|---|---|---|---|---|
| Synthetic Topogram 40 | $1.77 \times 10^{-2}$ | $1.51 \times 10^{-3}$ | 2.63 | 2.03 |
| Regenerated Topogram 48 | $1.41 \times 10^{-2}$ | $6.60 \times 10^{-4}$ | 1.46 | 1.07 |

Using the proposed topogram completion method described above may help achieve a more accurate topogram and significantly reduce the landmarks error. "Δ" represents the mean Euclidian distance and "Δy" represents the mean y distance. The Minimum Absolute Error (MAE) and the Mean Square Error (MSE) are in cm.

Due to privacy and health safety issues, medical imaging data is difficult to obtain, which creates a significant barrier for data driven analytics such as deep learning. The topogram prediction may be employed to generate realistic training data. The ability to spatially reposition the landmarks and generate a corresponding topogram is used to create a varied sampling for training. Parametrized X-ray images offer an approach to generate medical image training data. The spatial parametrization offers controlled perturbations such as generating data variations with lungs of certain sizes. For tasks such as marker detection, since the image manifold is smooth (i.e., linear transition of landmarks with no unrealistic movement, or jumps), it is possible to generate training data (for augmentation) together with annotations, by annotating the marker in one image and tracking it in the image domain as it is perturbed along the image manifold.

In one example of generating training data, the left lung bottom landmark, which is not part of the parametrization, is manually annotated in 50 synthetic X-ray images to be used for training data. For evaluation, 50 ground truth X-ray images may be manually annotated. To generate the augmented training dataset, 100 random perturbations are generated from the annotated parametrized images by allowing a selected marker to move within a certain range. Since the image manifold is smooth, as the position of the selected marker changes in the perturbed image, the annotated marker propagates in the same image accordingly using coefficient normed template matching.

Figure 5:
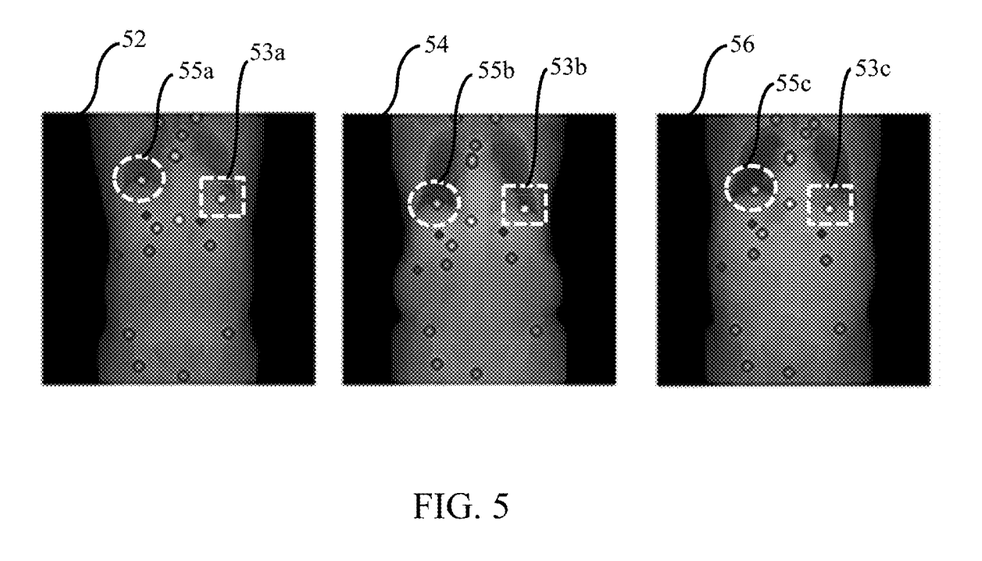
FIG. 5 shows three example generated perturbations of topogram images used to augment training data.

FIG. 5 shows three generated perturbations of parametrized topogram images 52, 54, 56 for three patients used to augment training data. Once parametrized topogram images of each patient is generated from surface data as discussed above, body marker locations are predicted using the machine-learned network as described above. To generate the perturbations of the generated parametrized topogram images, an internal landmark of the generated topogram is annotated. The internal landmark may not correspond to one of the body marker locations predicted by the machine-learned network. Next, one of the body markers predicted by the machine-learned network is identified and a random perturbed position of the identified predicted body marker 55 of the plurality of predicted body markers is created by moving the identified predicted body marker along an image manifold. The identified predicted body marker may be moved manually. Alternatively, the identified predicted body marker may be moved automatically using image transformation, such as translation, rotation, projection, and/or scaling. In this case, the marker may be moved automatically by the image processor in any direction within a certain distance range. Other now known or later developed image transformation techniques may be used.

A changed position of the annotated internal landmark 53 is propagated based on the random perturbed position of the identified predicted body marker 55. The propagation may be performed using coefficient normed template matching. A random perturbed parametrized image is then generated based on the changed position of the annotated first predicted body marker 53 and the random perturbed position of the second predicted body marker 55. In one embodiment, the changed position of the annotated first predicted body marker 53 and the random perturbed position of the second predicted body marker 55 may be input into the machine-learned network and the image processor may then generate the new perturbed parametrized image. In another embodiment, image transformation techniques may be used such that the image processor uses the new locations of the changed position of the annotated first predicted body marker 53 and the random perturbed position of the second predicted body marker 55, along with the originally generated topogram to generate the new perturbed parametrized image.

For example, for the patient in image 52 of FIG. 5, the left lung bottom internal landmark is first annotated. Then, a first predicted body marker is moved along the image manifold to create a random perturbed position of the first predicted body marker 55a. A changed position of the annotated internal landmark 53a is propagated based on the random perturbed position of the first predicted body marker 55a. A random perturbed parametrized image 52 is then generated based on the changed position of the annotated internal landmark 53a and the random perturbed position of the first predicted body marker 55a. The method is the same for the patients in images 54 and 56, where first predicted body markers are moved along the image manifold to create random perturbed positions of first predicted body markers 55b,55c and changed positions of the annotated internal landmarks 53b, 53c are propagated accordingly.

The steps of creating a random perturbed position of a first predicted body marker 55, propagating a changed position of the annotated internal landmark 53, and generating a random perturbed parametrized image may be repeated for different random perturbed positions to create a predetermined number of generated random perturbed parametrized images associated with the annotated internal landmarks of the generated topogram. In this regard, each time the first predicted body marker is changed to a new random position, a new resulting parametrized image is generated. Similarly, the annotating, the creating, the propagating, and the generating may be repeated a predetermined number of times for a predefined number of generated topograms. Thus, for each topogram a certain number of iterations of additional topograms are created. This allows the disclosed system to generate training data using the machine-learned network. The generated training data may be used to train another machine-learned network for a different task.

The disclosed method described above may be compared to a traditional translation method of forming training data to measure the usefulness of data generated using parametrized images. In a traditional translation method, such as a Fully Convolutional Network that is trained to regress the marker location, depicted as a Gaussian mask, from the X-ray image, an Adam optimizer with an initial learning rate of $10^{-3}$ is used. A baseline training dataset is created by augmenting 50 training images using 100 random translations. Table 2 below lists the error metrics as the two networks—the disclosed method of generating training data using perturbed parametrized images (p) and the traditional translation method (t)—are trained using the datasets for 25 epochs (after which they both overfitted). After only 5 epochs, the model trained with the parametrized training data (p) had a 0.99 cm mean error on the testing set, compared to 8.75 cm for the baseline (t). After 25 epochs, the baseline (t) has a mean error of 1.20 cm, while the network trained on data with parametrized perturbations (p) has a much lower 0.68 cm error.

TABLE 2

| Epoch | MSE(p) | MSE(t) | Δ(p) | Δ(t) |
|---|---|---|---|---|
| 1 | $6.64 \times 10^{-4}$ | $2.47 \times 10^{-3}$ | 4.53 | 9.17 |
| 5 | $4.04 \times 10^{-4}$ | $6.76 \times 10^{-4}$ | 0.99 | 8.75 |
| 10 | $3.50 \times 10^{-4}$ | $5.66 \times 10^{-4}$ | 0.93 | 2.67 |
| 15 | $3.47 \times 10^{-4}$ | $5.04 \times 10^{-4}$ | 0.64 | 1.97 |
| 20 | $3.59 \times 10^{-4}$ | $4.78 \times 10^{-4}$ | 0.74 | 1.28 |
| 25 | $3.50 \times 10^{-4}$ | $5.34 \times 10^{-4}$ | 0.68 | 1.20 |

Table 2 compares the translation training set (t) and parametrized training set (p). The metrics used are the MSE on the testing set and "Δ" represents the mean Euclidian distance in cm.

Figure 6:
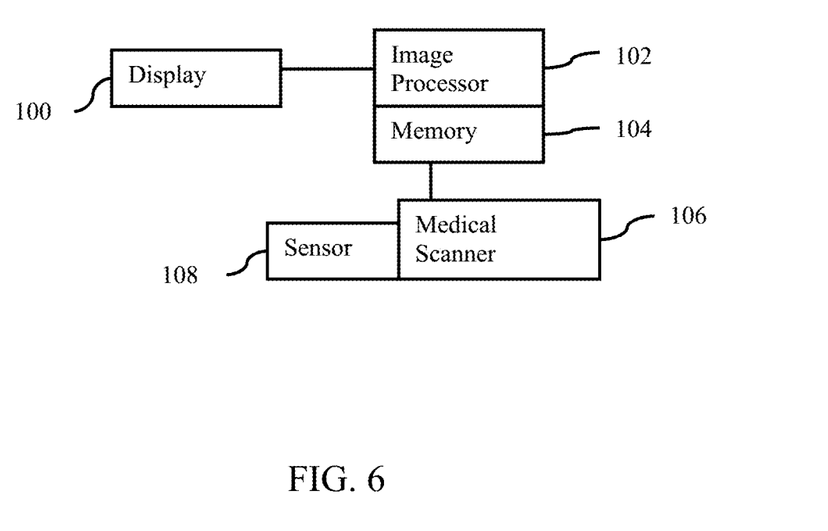
FIG. 6 is a block diagram of one embodiment of a system for anomaly detection.

FIG. 6 shows a medical imaging system for anatomical anomaly detection. The medical imaging system includes a display 100, memory 104, and image processor 102. The display 100, image processor 102, and memory 104 may be part of a medical scanner 106, a computer, server, workstation, or other system for image processing medical images from a scan of a patient. A workstation or computer without the medical scanner 106 may be used as the medical imaging system. The medical imaging system also includes a sensor 108 for sensing an outer surface of a patient.

Additional, different, or fewer components may be provided. For example, a computer network is included for remote anomaly detection, including topogram image generation of locally captured surface data, or for local anomaly detection and topogram image generation from remotely captured surface data. The network is applied as a stand-alone application on the workstation or a local device or as a service deployed on network (cloud) architecture. As another example, a user input device (e.g., keyboard, buttons, sliders, dials, trackball, mouse, or other device) is provided for user alteration or placement of one or more markers (e.g., landmarks).

The sensor 108 is a depth sensor. LIDAR, 2.5D, RGBD, stereoscopic optical sensor, or other depth sensor may be used. One sensor 108 is shown, but multiple sensors may be used. A light projector may be provided. The sensor 108 may include a separate processor for depth measurements from images, or the image processor 102 determines the depth measurements from images captured by the sensor 108.

The sensor 108 is directed to a patient. The sensor 108 may be part of or connected to the medical scanner 106 or is separate from the medical scanner 106.

The sensor 108 is configured to measure depths to the patient. The depths are distances from the sensor 108 or other location to the patient at various locations on the patient. Any sample pattern over the patient may be used. The sensor 108 outputs depth measurements and/or a surface image. The image processor 102 or another processor may fit a model to the sensor output to provide surface data. Alternatively, the sensor 108 outputs the surface data as the measurements.

The sensor measurements, fit shape model, surface data, network definition, features, machine-learned network, landmark images, topograms for a plurality of patients, detected anomaly images and/or other information are stored in a non-transitory computer readable memory, such as the memory 104. The memory 104 is an external storage device, RAM, ROM, database, and/or a local memory (e.g., solid state drive or hard drive). The same or different non-transitory computer readable media may be used for instructions and other data. The memory 104 may be implemented using a database management system (DBMS) and residing on a memory, such as a hard disk, RAM, or removable media. Alternatively, the memory 104 is internal to the processor 102 (e.g. cache).

The memory 104 may also store association data that corresponds one set of stored values to another set of stored values. For example, each topogram stored in the memory 104 may be associated with corresponding surface data of a patient. In another example, each of the stored topograms may correspond to and be associated with classification data. The classification data may be indicative of a type, or class, of patient. For example, one class may be defined by healthy patients (i.e., patients having no pathologies). Another class may be defined by patient size, body type, age, or gender. Any type of classification data may be used.

The instructions for implementing the training or application processes, the methods, and/or the techniques discussed herein are provided on non-transitory computer-readable storage media or memories, such as a cache, buffer, RAM, removable media, hard drive or other computer readable storage media (e.g., the memory 104). Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination.

In one embodiment, the instructions are stored on a removable media device for reading by local or remote systems. In other embodiments, the instructions are stored in a remote location for transfer through a computer network. In yet other embodiments, the instructions are stored within a given computer, CPU, GPU or system. Because some of the constituent system components and method steps depicted in the accompanying figures may be implemented in software, the actual connections between the system components (or the process steps) may differ depending upon the manner in which the present embodiments are programmed.

The image processor 102 is a control processor, general processor, artificial intelligence processor, digital signal processor, three-dimensional data processor, graphics processing unit, application specific integrated circuit, field programmable gate array, digital circuit, analog circuit, combinations thereof, or other now known or later developed device for processing medical image data. The image processor 102 is a single device, a plurality of devices, or a network. For more than one device, parallel or sequential division of processing may be used. Different devices making up the image processor 102 may perform different functions, such as applying different GANs, acquiring X-ray images, comparing images, matching surface data, or detecting anomalies. In one embodiment, the image processor 102 is a control processor or other processor of a medical diagnostic imaging system, such as the medical scanner 106. The image processor 102 operates pursuant to stored instructions, hardware, and/or firmware to perform various acts described herein.

The image processor 102 is configured to train a machine learning architecture. Based on a user provided or other source of the network architecture and training data, the image processor 102 learns features for encoders, decoders, discriminators, or other network parts to train the network. The result of the training is a machine-learned network or networks for topogram prediction and anomaly detection with or without landmark parameterization.

Alternatively or additionally, the image processor 102 is configured to apply one or more machine-learned networks. For example, a GAN is applied to surface data from the sensor or surface data stored in the memory 104. The machine-learned generative network is applied to surface information. Based on the previous training, the network generates a topogram in response to application of the surface data (e.g., depth information from measured depths). One network may output a landmark probability map (e.g., heatmap), and another network may output the topogram based on input of the landmark probability map. Both networks may receive depth information for the outside of the patient as inputs. As another example, the image processor 102 is configured to generate the topogram using a GAN having been trained using healthy patients.

The image processor 102 is configured to generate an image. The topogram output from the GAN may be an image. Alternatively, the scalar values forming the topogram are mapped to display values. Annotations or graphics, such as for the landmarks, may be added to the image. The image processor 102 may generate the topogram based on the surface data, either acquired by the sensor 108 or stored in the memory 104, and a plurality of topograms stored on the memory 104. The image processor 102 may access the memory 104 to retrieve data stored on the memory 104, such as stored surface data and/or stored topograms.

The image processor 102 is configured to acquire an X-ray image of the patient. The X-ray image may be acquired by an X-ray device coupled to the medical imaging system. In this embodiment, the image processor 102 may send instructions to the medical scanner 106 to acquire the X-ray image. The medical scanner 106 may then capture the X-ray image of the patient. The X-ray image may also be acquired by the image processor 102 accessing the X-ray image from a stored location, such as the memory 104.

The image processor 102 is configured to compare the generated predicted patient topogram with the acquired X-ray image, and detect, based on the comparison, an anatomical anomaly between the generated predicted patient topogram and the acquired X-ray image, as discussed above with regard to FIG. 2.

The image processor 102 may be configured to match data sets stored in the memory 104. For example, the image processor 102 may match the surface data of one patient to the corresponding surface data of other patients associated with the plurality of topograms stored in the memory 104. The image processor 102 may then predict a patient topogram based on the matched surface data.

The display 100 is a CRT, LCD, projector, plasma, printer, tablet, smart phone or other now known or later developed display device for displaying the output, such as a topogram or an image of the detected anatomical anomaly, as shown in FIG. 2, column (c). The display 100 may display a medical image topogram generated from the depth information, an actual acquired topogram (i.e., real X-ray), and an image showing the difference between the generated topogram and the real X-ray achieved by subtraction, either alone or side by side. The detected anatomical anomaly may be displayed such that the anomaly is highlighted to stand out from the rest of the image or images.

The medical scanner 106 is a medical diagnostic imaging system configured to scan a volume of a patient and generate anatomical information from the scan. The medical scanner 106 is a CT, MR, PET, SPECT, X-ray, or ultrasound scanner.

The medical scanner 106 is configured to generate anatomical information. The configuration uses settings for one or more parameters, such as an X-ray source voltage, table position and/or range of movement, gantry position and/or range of movement, focus, field of view, scan density, detector thresholds, transmission sequence, image processing settings, filtering settings, or image generation settings. Based on a topogram generated from the surface data rather than scanning by the medical scanner 106, one or more settings of the medical scanner 106 are set. The patient is imaged by the medical scanner 106 using the settings. In alternative embodiments, scan data from the medical scanner 106 is used to determine the surface data, such as by fitting a statistical shape model that includes a skin mesh to the scan data.

Various improvements described herein may be used together or separately. Although illustrative embodiments of the present invention have been described herein with reference to the accompanying drawings, it is to be understood that the invention is not limited to those precise embodiments, and that various other changes and modifications may be affected therein by one skilled in the art without departing from the scope or spirit of the invention.

What is claimed is:

1. A method for anomaly detection in a medical imaging system, the method comprising:
    capturing, with a sensor, first surface data representing an outer surface of a patient;
    generating, by an image processor, a topogram of the patient by a machine-learned network in response to input of the first surface data to the machine-learned network, the machine-learned network having been trained with surface data from healthy patients, the generated topogram representing an internal anatomy of the patient as a projection through the patient;
    acquiring an X-ray image of the patient;
    comparing, by the image processor, the generated topogram with the acquired X-ray image; and
    detecting, by the image processor based on the comparison, an anomaly of the patient from the comparison between the generated topogram and the acquired X-ray image.

2. The method of claim 1 wherein capturing comprises capturing with the sensor being a depth sensor.

3. The method of claim 1 wherein capturing comprises capturing with the sensor being a camera where the first surface data comprises optical measurements.

4. The method of claim 1 wherein generating further comprises fitting a statistical shape model to the first surface data, the first surface data comprising (a) depths from the fit statistical shape model and (b) a projection of the outer surface or a thickness.

5. The method of claim 1 wherein the machine-learned network was trained as a machine-learned generative adversarial network comprising a fully convolutional network with an encoder and a decoder.

6. The method of claim 1 wherein the generated topogram is a parametrized image having a plurality of predicted body markers, the plurality of predicted body markers representing spatial parameters of the internal anatomy of the patient.

7. The method of claim 6 further comprising regenerating the topogram based on the plurality of predicted body markers.

8. The method of claim 7 wherein regenerating the topogram comprises:
    adjusting, based on the comparison of the generated topogram with the acquired X-ray image, the plurality of predicted body markers such that the generated topogram matches the acquired X-ray image where the generated topogram and the acquired X-ray image overlap; and regenerating the topogram based on the adjusted body markers.

9. The method of claim 6 further comprising generating, with the machine-learned network, perturbations of the generated topogram as training data, the generation of the perturbations comprising:
annotating an internal landmark of the generated topogram;
creating a random perturbed position of a first predicted body marker of the plurality of predicted body markers by moving the first predicted body marker along an image manifold;
propagating a changed position of the annotated internal landmark based on the random perturbed position of the first predicted body marker; and
generating a random perturbed parametrized image based on the changed position of the annotated internal landmark and the random perturbed position of the first predicted body marker,
wherein the creating, the propagating, and the generating are repeated for different random perturbed positions to create a predetermined number of generated random perturbed parametrized images associated with the annotated internal landmark of the generated topogram.

10. The method of claim 9 wherein the annotating, the creating, the propagating, and the generating are repeated a predetermined number of times for a predefined number of generated topograms.

11. The method of claim 9 wherein the creating comprises moving the first predicted body marker within a predefined distance range along the image manifold.

12. The method of claim 9 wherein the propagating comprises propagating the changed position of the annotated internal landmark using coefficient normed template matching.

13. A method for detecting anatomical anomalies in a medical imaging system, the method comprising:
capturing, with a sensor, surface data representing an outer surface of a patient;
generating, by an image processor, a spatial marker map by a first machine-learned network, the first machine-learned network outputting the spatial marker map in response to input of the surface data to the first machine-learned network;
generating, by an image processor, a topogram by a second machine-learned network in response to input of the surface data and the spatial marker map to the second machine-learned network, the topogram representing an internal anatomy of the patient as a projection through the patient;
acquiring an X-ray image of the patient;
comparing, by the image processor, the generated topogram with the acquired X-ray image; and
detecting, by the image processor based on the comparison, an anatomical anomaly between the generated topogram and the acquired X-ray image.

14. The method of claim 13 further comprising iteratively using the first and second machine-learned networks, the first machine-learned network outputting the spatial marker map in response to input of the topogram and the surface data.

15. The method of claim 13 wherein the generated topogram is a parametrized image having a plurality of predicted body markers, the plurality of predicted body markers representing spatial parameters of the internal anatomy of the patient, and further comprising regenerating the topogram based on the plurality of predicted body markers, wherein regenerating comprises:
adjusting, based on the comparison of the generated topogram with the acquired X-ray image, the plurality of predicted body markers such that the generated topogram matches the acquired X-ray image where the generated topogram and the acquired X-ray image overlap; and
regenerating the topogram based on the adjusted body markers.

16. The method of claim 13 wherein the generated topogram is a parametrized image having a plurality of predicted body markers, the plurality of predicted body markers representing spatial parameters of the internal anatomy of the patient, and further comprising generating with the first and second machine-learned networks perturbations of the generated topogram as training data, the generation of the perturbations comprising:
annotating an internal landmark of the generated topogram;
creating a random perturbed position of a first predicted body marker of the plurality of predicted body markers by moving the first predicted body marker along an image manifold;
propagating a changed position of the annotated internal landmark based on the random perturbed position of the first predicted body marker; and
generating a random perturbed parametrized image based on the changed position of the annotated internal landmark and the random perturbed position of the first predicted body marker,
wherein the creating, the propagating, and the generating are repeated for different random perturbed positions to create a predetermined number of generated random perturbed parametrized images associated with the annotated internal landmark of the generated topogram.

17. A medical imaging system for anatomical anomaly detection, the medical imaging system comprising:
a memory configured to store surface data of a patient and a plurality of topograms, each topogram of the plurality of topograms being associated with corresponding surface data of other patients;
an image processor configured to generate a predicted patient topogram based on the surface data of the patient and the plurality of topograms, acquire an X-ray image of the patient, compare the generated predicted patient topogram with the acquired X-ray image, and detect, based on the comparison, an anatomical anomaly between the generated predicted patient topogram and the acquired X-ray image; and
a display configured to display the detected anatomical anomaly.

18. The medical imaging system of claim 17 wherein the image processor, in order to generate the predicted patient topogram, is configured to match the surface data of the patient to the corresponding surface data of other patients associated with the plurality of topograms and predict the patient topogram based on the matched surface data.

19. The medical imaging system of claim 17 wherein the plurality of stored topograms correspond to a class defined by healthy patients.

20. The medical imaging system of claim 17 wherein the image processor generates the predicted patient topogram by a machine-learned network in response to input of the surface data of the patient and the plurality of topograms to the machine-learned network.

* * * * *